US012741054B2

(12) United States Patent
Geysoğlu et al.

(10) Patent No.: US 12,741,054 B2
(45) Date of Patent: Sep. 22, 2026

(54) DEVELOPMENT OF EGG WHITE BASED NANOFIBER TREATMENT MATERIAL

(71) Applicant: SÜLEYMAN DEMIREL ÜNİVERSİTESİİDARİVE MALİİŞLER DAİRE BAŞKANLIĞI GENEL SEKRETERLIK, Isparta (TR)

(72) Inventors: Mustafa Geysoğlu, Isparta (TR); Funda Cengiz Çallioğlu, Isparta (TR); Kanat Gülle, Isparta (TR)

(73) Assignee: SÜLEYMAN DEMIREL ÜNIVERSITESI IDARI VE MALI ISLER DAIRE BASKANLIGI GENEL SEKRETERLIK, Isparta (TR)

( * ) Notice: Subject to any disclaimer, the term of this patent is extended or adjusted under 35 U.S.C. 154(b) by 185 days.

(21) Appl. No.: 18/860,656

(22) PCT Filed: Dec. 11, 2023

(86) PCT No.: PCT/TR2023/051506
§ 371 (c)(1),
(2) Date: Oct. 27, 2024

(87) PCT Pub. No.: WO2024/144634
PCT Pub. Date: Jul. 4, 2024

(65) Prior Publication Data

US 2025/0288716 A1 Sep. 18, 2025

(30) Foreign Application Priority Data

Dec. 30, 2022 (TR) ............................... 2022/021580

(51) Int. Cl.
*A61L 26/00* (2006.01)

(52) U.S. Cl.
CPC ....... *A61L 26/0028* (2013.01); *A61L 26/0014* (2013.01); *A61L 26/0019* (2013.01)

(58) Field of Classification Search
CPC ............. A61L 26/0028; A61L 26/0014; A61L 26/0019
See application file for complete search history.

(56) References Cited

U.S. PATENT DOCUMENTS

2021/0154206 A1 5/2021 Sheffield

FOREIGN PATENT DOCUMENTS

| | | | |
|---|---|---|---|
| CN | 107837381 | A1 | 3/2018 |
| CN | 108261557 | A1 | 7/2018 |
| CN | 111388576 | A1 | 7/2020 |
| GB | 2572566 | A1 | 10/2019 |

OTHER PUBLICATIONS

Jalili-Firoozinezhad, S., Filippi, M., Mohabatpour, F., Letourneur, D., & Scherberich, A. (2020). Chicken egg white: Hatching of a new old biomaterial. Materials Today. doi:10.1016/j.mattod.2020.05.022.

International Search Report and Written Opinion for International Application No. PCT/TR2023/051506, mailing date of Jul. 7, 2024.

*Primary Examiner* — Trevor Love
(74) *Attorney, Agent, or Firm* — Fresh IP PLC; Clifford D. Hyra; Aubrey Y. Chen

(57) ABSTRACT

Disclosed herein is the production of biopolymers and egg white active ingredient-based nanofibrous materials for use in the treatment of second-degree burns. Specifically disclosed is the design, production, characterization, and in-vivo applications of a double-layer nanofibrous burn wound material with different functional properties are provided. Electrospinning method may be used in the production of the material.

12 Claims, No Drawings

DEVELOPMENT OF EGG WHITE BASED NANOFIBER TREATMENT MATERIAL

This application is a National Phase entry of International Application No. PCT/TR2023/051506 under § 371 and claims the benefit of Turkish Patent Application No. TR2022/021580, filed Dec. 30, 2022, which is hereby incorporated by reference in its entirety.

FIELD OF THE DISCLOSURE

The subject of the disclosure is related to the production of biopolymers and egg white active ingredient-based nanofibrous materials for use in the treatment of second-degree burns. In the disclosure, the design, production, characterization, and in-vivo applications of a double-layer nanofibrous burn wound material with different functional properties are provided. Electrospinning method was used in the production of the material.

BACKGROUND

Today, many methods and tools are used for the treatment of burn wounds. Although the care of burn wounds requires great attention, ideal dressings and dressing materials are especially important for the care of second-degree burns and rapid wound healing. An ideal healing or wound treatment material that contributes to the treatment should protect the burn wound from bacteria and foreign substances, absorb the fluid in the wound and keep the wound area moist, and should not contain toxic or allergenic substances. At the same time, it should be easily applied without damaging the wound and the surrounding skin, and then removed from the wound area without causing any damage during the replacement process. In addition, the mechanical strength of the treatment materials must be good. With this strength, it is essential that it will not interfere with the daily activities of the patient and will not cause any tearing, distortion or curling on the wound. However, there are burn wound dressings used in the state of the art. These dressings are aluminum film burn dressings used only to maintain body temperature when the burn wound first forms. These wound dressings are only intended to protect the wounded area. In addition, they comprise toxic active substances such as silver (Ag). In addition to protecting the wound, there are also commercial burn wound dressings that comprise harmless substances that accelerate its healing. These dressings are generally in the form of net, hydrogel or film, and the use of nanofiber or the addition of materials with different properties is not encountered. In addition to all this, the lack of materials comprising natural active ingredients, which are more accessible than chemicals or drugs in wound burn treatments, also poses a problem in the state of the art.

In the prior art document numbered CA2640197A1, a wound dressing is described. Said wound dressing comprises first and second absorbent layers of a fabric woven from viscose and polyester fibers. Each absorbent layer has an operative inner face and an operative outer face. Said wound dressing further comprises a third layer sandwiched between and bonded to the first and second absorbent layers. The third layer is in the form of cotton gauze. At least one embodiment of the invention does not comprise a layer formed from nanofibers or polymer in any way and does not comprise a method for making a wound dressing and a method for treating a wound.

The prior art document numbered U.S. Pat. No. 4,361,552A describes a wound or burn treatment method that involves covering the surface of the wound or burn with a cross-linked amniotic dressing. A wound dressing of amnion is provided, and the wound is treated to essentially become a more permanent dressing until it heals. Fresh amnion from any animal source is stabilized with glutaraldehyde solutions or any other fixing or tanning solution to cross-link its proteins.

In the prior art document numbered CN209392237U a facial burn wound dressing set is described. The burn patch includes a burn patch and an elastic mesh dressing. The burn patch is in contact with the inside of the elastic mesh dressing; the burn patch is in the form of a mask formed with two open eyes, a nose open hole and a mouth open hole. The burn patch of the facial burn wound dressing set is made in the shape of a face mask.

In addition, the burn tag includes a dressing layer and a cotton pad layer, one side of the cotton pad layer is fixedly attached to the dressing layer, and the other side of the cotton pad layer is in contact with the inner side of the elastic mesh. It is structured to be used only as a wrapping material.

The prior art document numbered CN108404191A describes graphene oxide/lidocaine sponge dressing and the preparation method thereof. Medical sponge dressing combines the excellent performance of graphene oxide, lidocaine, polyvinyl alcohol and the like, and has the structure of fast liquid absorption, large liquid absorption amount, large moisture retention amount, antibacterial activity, analgesia, and flexibility; a dressing developed using graphene oxide and used in wounds and burns is described.

The prior art document numbered CN108261557A describes nanofiber membrane for wound healing and the preparation method and application thereof. It uses polycaprolactone, gelatin and nagelschmidtite biological ceramics as raw materials, and a mixed electrospinning technique is used to prepare the composite nanofiber membrane used for wound healing. The composite nanofiber membrane can visibly shorten the healing time of soft tissue chronic wounds, especially diabetes mellitus wounds, and promote angiogenesis, epidermis regeneration and collagen formation in wound areas. It is structured to reduce the inflammatory responses of chronic wounds and promote wound healing for soft tissue.

The prior art document numbered 2016/11396 describes a medical wound dressing comprising a cross-linking agent, natural and/or leaf polymers, and thin exit submucosa, which accelerates the healing process of various wounds and burn wounds, for use in the healthcare sector. Since it comprises growth factors effective in wound healing such as TGF-β, FGF-2, VEGF and EGF in certain doses, the sponge structure serves as a scaffold for new tissue formation while natural re-tissue is repaired. With cellular stimulation, host cells provide new vascular structures, surrounding differentiation and region-specific tissue regeneration.

In the prior art document numbered 2015/17118, an antibacterial PCL/Chitosan wound dressing material is described. It is a composite-biocompatible wound dressing material used in the use of artificial tissue scaffolds, which are considered as an alternative solution instead of tissue transplantation for the treatment of tissue damage, and specifically for burn cases. The developed composite-biomaterial is structured to support the healing process of tissue damage above the critical defect size.

There is no study, national or foreign, regarding the production, detailed characterization, in-vitro and in-vivo applications of wound treatment material comprising polyacrylic acid, polycaprolactone and egg white protein active ingredients in its structure.

SUMMARY

One objective of at least one embodiment of the invention is to develop nanofibrous wound treatment material comprising egg white active ingredient for the healing of burn wounds and to provide healing of second-degree burn wounds with the material produced by electrospinning method.

Another objective of at least one embodiment of the invention is to absorb wound exudate and keep the wound moist by means of the polyacrylic acid (PAA), the first of the two layers, which is a nanofibrous wound treatment material particularly developed for use in the treatment of second-degree burn wounds.

Another objective of at least one embodiment of the invention is to accelerate wound healing by adding polycaprolactone (PCL) polymer, which does not stick to the wound and does not interfere with the daily life of the patient due to its high strength, and egg white as a wound healing active ingredient, in the second layer in contact with the wound.

Another objective of at least one embodiment of the invention is to accelerate the healing process with burn treatment material comprising PAA, PCL and egg white protein as a healing active ingredient and developed by electrospinning method.

Another objective of at least one embodiment of the invention is to obtain a biomedical material that is environmentally friendly, has sustainable potential and has high added value, by means of the developed nanofibrous burn treatment material and the polymers and active ingredients used.

Another objective of at least one embodiment of the invention is to develop the burn wound material comprising nanofibrous egg white protein active ingredient for use in the treatment of burn wounds. The electrospinning method was used in the production of the nanofibrous material, and the design, production and characterization of the two-layer nanofibrous wound burn material was carried out. The first layer of the developed nanofibrous wound burn material consists of polyacrylic acid (PAA) based nanofibers with super absorbent properties, which are expected to absorb wound exudate and keep the injured area moist. In the production of the second layer in contact with the wound, polycaprolactone (PCL) polymer was used, taking into account its flexibility, high strength and non-adhesion to the wound due to its hydrophobic structure. In this layer, protein-based egg white was preferred as the wound healing active ingredient. As a result of histopathological analysis of the two-layer nanofibrous surfaces produced according to at least one embodiment of the invention, it has been determined that the nanofibrous wound treatment material has the potential to accelerate the healing of second-degree burn wounds.

DETAILED DESCRIPTION

In one study of at least one embodiment of the invention, the design, production, and characterization of a two-layer nanofibrous wound treatment material was carried out. Later, in-vivo studies were conducted on experimental animals to determine the burn wound healing performance of the developed nanofibrous material. The subject of at least one embodiment of the invention describes the burn treatment material comprising polyacrylic acid (PAA) and polycaprolactone (PCL) polymers and egg white as active ingredient, which accelerate the healing process in burn treatment.

In experimental studies, optimization studies were first carried out in terms of both fiber drawing performance and fiber morphology. Then, in nanofiber production by electrospinning method, solution properties such as conductivity, surface tension and viscosity, which are closely related to fiber spinning performance and fiber morphology, were determined. Electrospinning technique is an approach used to produce nanofibers. In this method, the polymer solution/melt is subjected to an electrical field. Under the influence of the electric field, the fibers are scattered and thin, dry polymeric fibers with nanometer diameters are formed on the collector surface. In this method, firstly the polymer solution is prepared and placed into the syringe. With the help of a feeding pump, a droplet of polymer solution is formed at the tip of the needle/apparatus connected to the syringe. In this case, the droplet stands at the tip of the apparatus in balance with its own surface tension and gravitational force. When the applied electrical potential exceeds the surface tension of the droplet, a polymer jet exits the apparatus and begins to move towards the opposite collector. During this movement of the polymer jet, the solvent moves away and the polymer jet becomes longer and thinner.

For the first layer in the production of nanofibrous wound treatment material, the PAA-based superabsorbent nanofibrous layer was produced under optimum conditions and then cross-linked. In cross-linking studies, physical cross-linking with heat was applied and water solubility was prevented. This layer of wound treatment material is important for its ability to absorb wound exudate and keep the wound surface moist. Then, the surface of the cross-linked superabsorbent PAA nanofiber layer was coated with PCL-based nanofibers comprising egg white to form the second layer.

PCL polymer is an ideal polymer for wound treatment material due to its features such as being biocompatible and biodegradable, flexible and durable. Additionally, it is preferred because it will not stick to the wound due to its hydrophobic structure.

In the study, egg white protein is used as the main active ingredient in the nanofibrous surface produced as a wound treatment material and is used in the treatment of second-degree burn wounds by using the properties of proteins, such as growth, reproduction and self-repair processes, which are the basic characteristics of life.

After the optimization studies were completed and nanofiber production was finalized, the morphological, chemical and thermal characterizations of PCL-based nanofibers were completed by SEM, FT-IR, TGA, DSC, DTG and XRD analyses. Then, the release performance of the active substance was determined from the produced nanofibers. After the optimization studies were carried out and the characterization processes were completed, water vapor permeability analysis was performed on the two-layer nanofibrous surfaces.

In the final stage of the study, in-vivo analyses of the two-layer produced nanofibrous surfaces were performed on experimental animals and the healing performance of at least one embodiment of the invention on second-degree burn wounds was evaluated histopathologically. As a result of histopathological analysis, it was determined that nanofibrous wound treatment material has the potential to accelerate the healing of second-degree burn wounds.

At least one embodiment of invention is a burn treatment material developed by electrospinning method for use in burn treatments and comprises polyacrylic acid (PAA), polycaprolactone (PCL) and protein. The protein used is the active ingredient of egg white.

Electrospinning method was used to obtain burn treatment and healing materials. In this method, a solution of polyacrylic acid, ethanol and pure water is prepared to form the first layer. Then, the solution is taken into the syringe and the solution is injected through the syringe needle with high voltage by applying pressure with the pump. After the fibrous structure accumulates on the collector plate, the first layer is formed by physical cross-linking with heat. The second layer is formed on top of the first layer lying on the collector layer. For this purpose, polycaprolactone, protein and chloroform: DMF solution is prepared. Polycaprolactone was used as polymer, egg white active ingredient was used as protein, and chloroform and DMF (dimethylformamide) were used as solvents. Then, the prepared solution is taken into the syringe and the solution is injected through the syringe needle with high voltage by applying pressure with the pump. By combining the fibrous structure with a polyacrylic acid-based nanofiber layer on the collector plate, the production of a two-layer burn treatment material is completed.

At least one embodiment of invention is a burn treatment material developed by electrospinning method for use in second-degree burn treatments and comprises polyacrylic acid (PAA), polycaprolactone (PCL) and protein. The protein used is the active ingredient of egg white. The subject of at least one embodiment of the invention is the electrospinning method, which is a method of obtaining burn treatment material developed by the electrospinning method for use in burn treatments. To prepare the first layer, a solution of polyacrylic acid, ethanol and pure water is prepared and the solution is taken into a syringe. After the syringe is taken to the pump that feeds it into the system, a polymer solution droplet is created at the tip of the needle connected to the syringe with the feeding pump. By applying electrical potential, the surface tension of the droplet increases and the solution droplet becomes longer and thinner. After the fibrous droplets accumulate on the collector plate, the accumulated fibers are physically cross-linked with heat and left on the collector plate. The second layer is created on top of the first layer produced. After preparing the polycaprolactone, protein and chloroform: DMF solution, the solution is taken into a syringe. The syringe is taken into the pump that feeds it into the system, and a polymer solution droplet is formed at the tip of the needle connected to the syringe with the feeding pump. By applying electrical potential, the surface tension of the droplet increases and the solution droplet becomes longer and thinner. As the fibrous droplets accumulate on the collector plate, the first layer and the second layer are combined on the collector plate.

In this method, firstly, the polymer solution consisting of ethanol, pure water and polyacrylic acid, which will form the first layer, is prepared and placed into the syringe. With the help of a feeding pump, a droplet of polymer solution is formed at the tip of the needle/apparatus connected to the syringe. In this case, the droplet stands at the tip of the apparatus in balance with its own surface tension and gravitational force. Then, electrical potential is started to be given to the system with the help of the power supply. When the applied electrical potential exceeds the surface tension of the droplet, a polymer jet exits the apparatus and begins to move towards the opposite collector. During this movement of the polymer jet, the solvent moves away, and the polymer jet becomes longer and thinner. When the polymer jet reaches the collector, the solvent is completely removed and dry, nanometer diameter fibers remain on the collector. The last step of the nanofiber formation phase with the electrospinning method is the solidification of the sprayed polymer solution in the form of nanofibers. At this stage, the polymer jet reaches the collector and settles on the surface. The fibers reaching the collector are structures in the form of a two-dimensional nonwoven surface consisting of staple fibers, completely removed from the solvent. After this, the first layer, created using heat, is cross-linked and placed on the collector plate. Following the same procedures, a solution comprising polycaprolactone, chloroform: DMF and egg white active ingredient protein is prepared to create the second layer. Then, it is taken into a syringe and the exact same procedure is repeated. This time, the second layer is formed on top of the first layer comprising polyacrylic acid on the collector material. Thus, second degree burn treatment material is prepared.

In the formation step of the first layer, the solution content comprises 5% polyacrylic acid by weight and a total of 95% pure water and ethanol by weight. The solution used in the preparation of the second layer comprises 7% polycaprolactone by weight, 9% egg white active ingredient by weight, and a total of 84% solvent (chloroform and DMF) by weight. According to a different preferred embodiment of the invention, the solvent that constitutes 84% by weight of the solution forming the second layer is 80% by weight chloroform and 20% by weight is DMF.

According to a different preferred embodiment of the invention, the solvent that constitutes 95% by weight of the solution forming the first layer is 70% by weight pure water and 30% by weight is ethanol.

The invention claimed is:

1. Second degree burn treatment material comprising:

polyacrylic acid (PAA), polycaprolactone (PCL), and protein comprising egg white active ingredient protein, wherein the second degree burn material is produced by an electrospinning method, and wherein the second degree burn material is used in burn treatments.

2. Second degree burn treatment material according to claim 1, wherein the PAA comprises 5% by weight polyacrylic acid, the PCL comprises 7% by weight polycaprolactone, and the protein comprises 9% by weight egg white active ingredient protein.

3. A method of producing second-degree burn treatment material via electrospinning, the method comprising:

preparing a solution with polyacrylic acid and solvent, intaking the solution into a syringe, taking the syringe to a pump that feeds into a system, creating a polymer solution droplet at a tip of a needle connected to the syringe with the pump, increasing the surface tension of the droplet thereby making the solution droplet longer and thinner by applying electrical potential, accumulating fibrous droplets on a collector plate, physically cross-linking of the accumulated fibers with heat, preparing an additional solution with polycaprolactone, protein, and additional solvent, intaking the additional solution into an additional syringe, taking the additional syringe to the pump that feeds it-into the system, creating another polymer solution droplet at the tip of the needle connected to the syringe with the pump, increasing the surface tension of the another polymer solution droplet thereby making the another polymer solution droplet longer and thinner by applying electrical potential, accumulating fibrous droplets on the collector plate, and joining the first layer and the second layer on the collector plate, wherein the protein comprises egg white active ingredient protein, and wherein the second-degree burn treatment material is used in burn treatments.

4. Method of producing second-degree burn treatment material according to claim 3, wherein the polyacrylic acid is 5% polyacrylic acid by weight.

5. Method of producing second-degree burn treatment material according to claim 3, wherein the solvent is 95% total by weight.

6. Method of producing second-degree burn treatment material according to claim 5, wherein the 95% by weight solvent comprises 70% pure water by weight.

7. Method of producing second-degree burn treatment material according to claim 5, wherein the 95% by weight solvent comprises 30% ethanol by weight.

8. Method of producing second-degree burn treatment material according to claim 3, wherein the polycaprolactone is 7% polycaprolactone by weight.

9. Method of producing second-degree burn treatment material claim 3, wherein the egg white active ingredient is 9% by weight.

10. Method of producing second-degree burn treatment material according to claim 3, wherein the additional solvent in is 84% by weight.

11. Method of producing second-degree burn treatment material according to claim 10, wherein the 84% by weight additional solvent comprises 80% chloroform by weight.

12. Method of producing second-degree burn treatment material according to claim 10, wherein the 84% by weight additional solvent comprises 20% DMF by weight.

* * * * *